United States Patent
Dziecielewski et al.

(10) Patent No.: US 8,531,660 B2
(45) Date of Patent: Sep. 10, 2013

(54) SUBSTRATE FOR SURFACE ENHANCED RAMAN SCATTERING STUDIES

(75) Inventors: Igor Dziecielewski, Warsaw (PL); Robert Holyst, Warsaw (PL); Agnieszka Kaminska, Sulejowek (PL); Sylwester Porowski, Warsaw (PL); Tadeusz Suski, Warsaw (PL); Jan Weyher, Warsaw (PL)

(73) Assignees: Instytut Chemi Fizycznej Polskiel Akademii Nauk, Warsaw (PL); Instytut Wysokich Cisnien Polskiej Akademii Nauk, Warsaw (PL)

( * ) Notice: Subject to any disclaimer, the term of this patent is extended or adjusted under 35 U.S.C. 154(b) by 377 days.

(21) Appl. No.: 13/051,618

(22) Filed: Mar. 18, 2011

(65) Prior Publication Data
US 2011/0235031 A1    Sep. 29, 2011

(30) Foreign Application Priority Data

Mar. 23, 2010    (PL) .......................... 390798

(51) Int. Cl.
    G01J 3/44        (2006.01)
(52) U.S. Cl.
    USPC ........................................... 356/301
(58) Field of Classification Search
    USPC ........................................... 356/301
    See application file for complete search history.

(56) References Cited

U.S. PATENT DOCUMENTS

| | | | |
|---|---|---|---|
| 6,329,215 B1 | 12/2001 | Porowski et al. | |
| 7,583,379 B2 | 9/2009 | Zhao et al. | |
| 7,586,601 B2 | 9/2009 | Ebstein | |
| 7,595,872 B2 | 9/2009 | Premasiri et al. | |
| 7,639,356 B2 | 12/2009 | Prokes et al. | |
| 7,715,003 B2 | 5/2010 | Mazur et al. | |
| 7,867,770 B2 | 1/2011 | Premasiri | |
| 2006/0275541 A1 | 12/2006 | Weimer | |
| 2008/0096005 A1 | 4/2008 | Premasiri | |
| 2008/0266555 A1 | 10/2008 | Murphy et al. | |
| 2008/0285024 A1 | 11/2008 | Prokes et al. | |
| 2009/0279085 A1 | 11/2009 | Ebstein | |
| 2010/0035412 A1* | 2/2010 | Samuelson et al. | 438/478 |
| 2010/0129623 A1 | 5/2010 | Johansson et al. | |
| 2010/0171948 A1 | 7/2010 | Mazur et al. | |
| 2010/0190661 A1* | 7/2010 | Lee et al. | 506/18 |

FOREIGN PATENT DOCUMENTS

| | | |
|---|---|---|
| PL | 183687 B1 | 12/1998 |
| WO | 2008/094089 A1 | 8/2008 |
| WO | 2009/035479 A1 | 3/2009 |

OTHER PUBLICATIONS

Search Report of P.390798, date of mailing Jun. 11, 2010.
Gang L. Liu et al. "Magnetic Nanocrescents as Controllable Surface-Enhanced Raman Scattering Nanoprobes for Biomolecular Imaging", Advanced Materials 2005, vol. 17, pp. 2683-2688.
Katrin Domke et al. "Tip-Enhanced Raman Spectra of Picomole Quantities of DNA Nucleobases et Au(111)"; J. Am. Chem. Soc, 2007, vol. 129, pp. 6708-6709.

(Continued)

*Primary Examiner* — Kara E Geisel
(74) *Attorney, Agent, or Firm* — Westerman Hattori Daniels & Adrian, LLP

(57) ABSTRACT

The invention relates to a substrate for surface enhanced Raman scattering studies comprising a semiconductor surface with whiskers, coated with metal selected from the group consisting of silver, gold, platinum, copper and/or alloys thereof, where the semiconductor mentioned is a gallium-containing nitride and essentially each whisker contains a linear defect inside.

21 Claims, 9 Drawing Sheets

(56) References Cited

OTHER PUBLICATIONS

Figure 1:
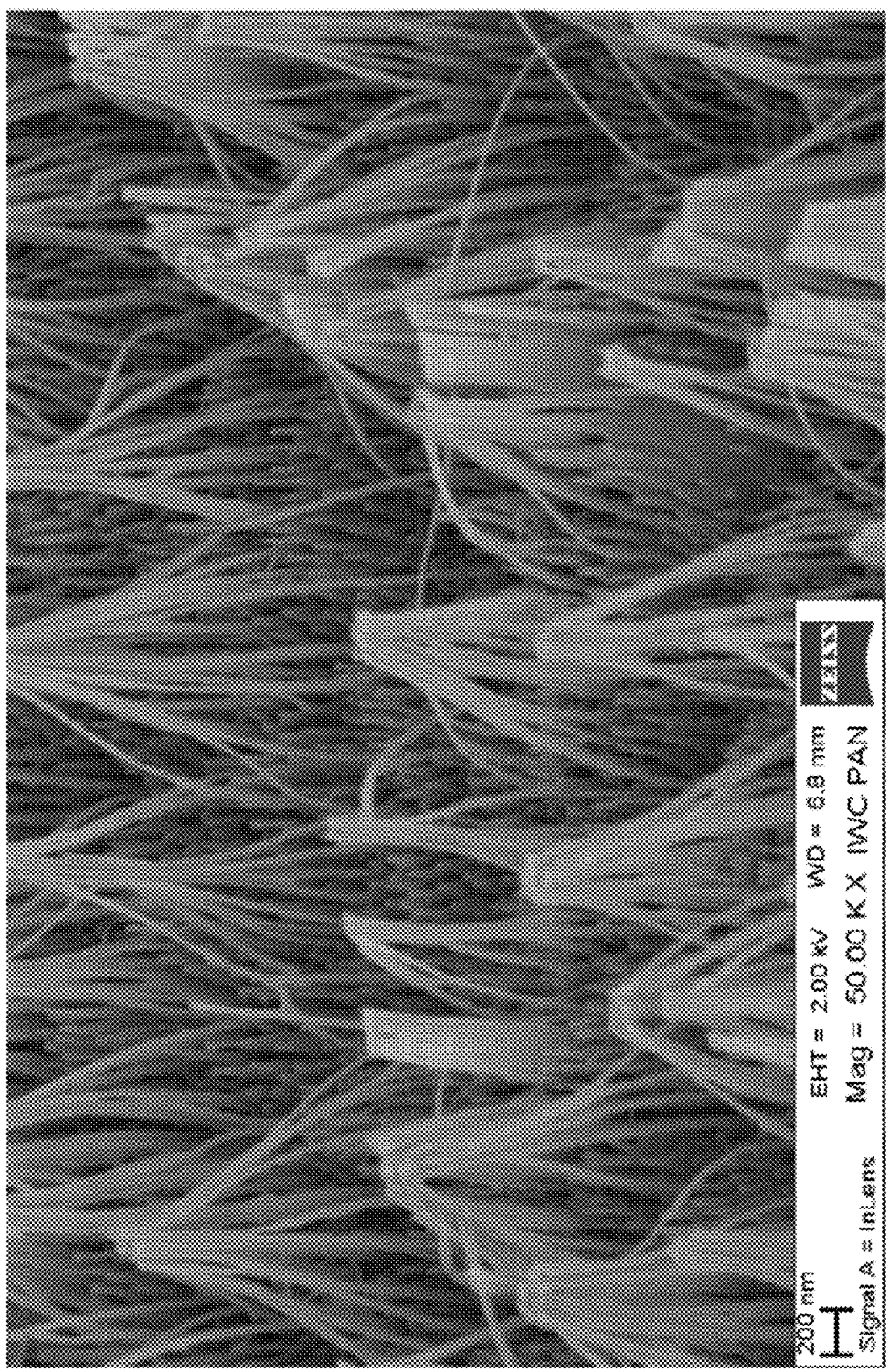

Katrin Kneipp et al. Single Molecule Detection Using Surface-Enhanced Raman Scattering (SERS)., Physical Review Letters, Mar. 3, 1997, vol. 78, No. 9, pp. 1667-1670.

Katrin Kneipp et al. "Ultrasensitive Chemical Analysis by Raman Spectroscopy" Chemical Reviews, 1999, vol. 99, No. 10, pp. 2957-2975.

Martin Moskovits, "Surface-Enhanced spectroscopy" Reviews of Modern Physics, vol. 57, No. 3, Part 1, Jul. 1985; pp. 783-828.

Patanjali Kambhampati et al. "On the chemical mechanism of surface enhanced Raman scattering: Experiment and theory" Journal of Chemical Physics; Mar. 22, 1998, vol. 108, No. 12, pp. 5013-5026.

Ray Gunawidjaja et al. "Freestanding 2D Arrays of Silver Nanorods", Advanced Materials; 2006; vol. 18, pp. 2895-2899.

Sangyeop Lee et al. "Surface-enhanced Raman scattering imaging of HER2 cancer markers overexpressed in single MCF7 cells using antibody conjugated hollow gold nanospheres"; Biosensors and Bioelectronics, vol. 24, 2009, pp. 2260-2263.

Shuming Nie et al. "Probing Single Molecules and Single Nanoparticles by Surface—Enhanced Raman Scattering", Science, vol. 275, Feb. 21, 1997, http;//www.sciencemag.org, pp. 1102-1106.

Todd L. Williamson et al. "Porous GaN as a Template to Produce Surface-Enhanced Raman Scattering-Active Surface" J. Phys. Chem. B, 2005, vol. 109, pp. 20186-20191.

Tonya M. Herne et al. "Surface-Enhanced Raman Spectroscopy of Peptides: Preferential N-Terminal Adsorption on Colloidal Silver", J. Am. Chem Soc. 1991, vol. 113, pp. 846-854.

* cited by examiner

SUBSTRATE FOR SURFACE ENHANCED RAMAN SCATTERING STUDIES

The subject matter of the invention is a substrate for surface enhanced Raman scattering (SERS) studies, comprising a surface of a gallium-containing nitride, coated with metal selected from among gold, silver, platinum, copper and/or alloys thereof.

The surface enhanced Raman spectroscopy is a spectroscopic technique to measure intensity of light in ultraviolet, visible and near infrared spectral regions that is inelastically scattered on molecules adsorbed on surfaces of certain metals (e.g. Ag, Au or Cu) with nanometer roughness features (10-100 nm) [M. Moskovits, Rev. Mod. Phys., 57 (1985) 783; K. Kneipp, H. Kneipp, I. Itzkan, R. R. Dasari, M. S. Feld, Phys. Rev. Lett., 76 (1996) 2444; K. Kneipp, H. Kneipp, I. Itzkan, R. R. Dasari, M. S. Feld, Phys. Rev. Lett., 78 (1997) 1667; S. Nie, S. R. Emory, Science, 275 (1997) 1102]. It has been one of the most intensely developed spectroscopic techniques in recent decade, as it allows to enhance the effective Raman scattering cross section of molecules adsorbed on a metal surface by several orders of magnitude ($10^2$-$10^6$, and for certain systems even $10^8$-$10^{15}$ [K. Kneipp, H. Kneipp, I. Itzkan, R. R. Dasari, M. S. Feld, Phys. Rev. Lett., 76 (1996) 2444; K. Kneipp, H. Kneipp, I. Itzkan, R. R. Dasari, M. S. Feld, Phys. Rev. Lett., 78 (1997) 1667; S. Nie, S. R. Emory, Science, 275 (1997) 1102] as compared with the effective Raman scattering cross section of non-adsorbed molecules [M. Herne, A. M. Ahern, R. L. Garrell, J. Am. Chem. Soc., 113 (1991) 846; J. Thornton, R. K. Force, Appl. Spectrosc., 45 (1991) 1522].

The application area of SERS spectroscopy is very extensive with the most important applications in electrochemical studies, polymer chemistry, biologically active compounds and biological processes. At present, however, the SERS method gains a lot of attention mainly in biomedicine and genetics [S. Lee, H. Chon, M. Lee, Biosensors and Bioelectronics 24 (2009) 2260-2263].

The SERS signal enhancement depends on a number of factors, including the effective Raman scattering cross section, frequency of excitation radiation, chemical origin of a molecule, and primarily on the sort of metal surface whereon the molecule is adsorbed and on the degree of surface roughness. These roughness features, or in other words unevennesses, are responsible for the electromagnetic mechanism of enhancement that is the dominant SERS mechanism [P. Kambhampati, C. M. Child, M. C. Foster, A. Campion, J. Chem. Phys., 108 (1998) 5013]. The electromagnetic mechanism assumes that the intensity of both the incident and the scattered electromagnetic radiation is higher on the metal surface than inside the metal, which can be described with the following relationship:

$$I_R \sim (E_R(r,\omega_S))^2$$

where $E_R(r,\omega_S)$ is the total intensity of the field related to the adsorbed molecule.

The total intensity of the field related to the molecule adsorbed on the metal surface, $E_R(r,\omega_S)$, represents a sum of electromagnetic field intensities acting on an adsorbate being a dipole in the absence of roughness features ($E_{dip}(r,\omega_S)$) and the field produced by each roughness feature ($E_{sc}(r,\omega_S)$) [R. L. Garell, Anal. Chem., 61 (1989) 401A]. For normal Raman effect, ($E_{dip}(r,\omega_S)$) assumes a relatively low value because of low energies of the dipole-laser radiation interaction. In SERS, the roughness features are a source of additional, very high electromagnetic field ($E_{sc}(\omega_{SC})$) that acts directly on a molecule adsorbed on the metal surface giving rise to an enormous increase in $E_R$.

Despite that various substrates called also grounds or platforms, can be used, including for instance:
- appropriately porous surfaces fabricated in specific oxidation-reduction cycles (ORC),
- surfaces fabricated with microlithographic techniques, metal sputtering on various surfaces or polystyrene spheres, deposition of metal gold or silver nanoparticles on glass, silicon or ITO substrates,
- surfaces fabricated by chemical etching using acids or chemical reduction of metal salts (formation of colloids), there is still a problem of achieving surfaces yielding a strong spectrum enhancement and its reproducibility at each point of the surface. They are extremely important properties of active surfaces for SERS measurements, especially considering the application of the technique in biomedical studies or biosensor design [Liu, G. L., Lu, V., Kim, J., Doll, J. C., and Lee, L. P. Adv. Mater. 2005 17 2683; Domke, K. F., Zhang, D., and Pettinger, B. J. Am. Chem. Soc. 2007 129 6708; Gunawidjaja, R., Peleshanko, S., Ko, H., and Tsukruk, V. V. Adv. Mater. 2008 20 1544].

SERS is a technique where measurement conditions must be perfectly controlled if the results to be obtained are to be reproducible, conceivable and true. This will be assured by, inter alia, a method to fabricate reproducible, stable and sensitive substrates for SERS measurements.

In spite of a vast number of literature reports and patent applications there is no method at present that would guarantee reproducibility of SERS spectra for a given surface morphology. Well-known are nanoparticle-based surfaces for SERS measurements. Also nanowires are used, including those based on gallium nitride. Here are the examples of essential patent applications in the field:

The subject matter of the US patent application no. US2008/0096005 A1 "Nanostructured substrate for surface enhanced Raman scattering" are silicon, aluminium oxide or titanium dioxide surfaces covered with silver or gold nanoparticles with size ranging from 40 nm to 120 nm. For E. coli bacteria adsorbed on one of the exemplary substrates an enhancement factor of $2 \times 10^4$ has been obtained, the aspect of reproducibility of fabricated substrates has not, however, been studied.

The subject matter of the US patent application no. US 2006/0275541 A1 "System and method for fabricating substrate surfaces for SERS and apparatuses utilizing same" is a substrate for detection of biological molecules with SERS technique that comprises controlled and strictly defined vapour deposition of thin gold or silver films with PVC (Physical Vapour Deposition, i.e., physical deposition from gas phase) method on glass, liquid crystal or polymer surfaces. The authors report an enhancement factor of the order of $10^{10}$ for Bacillus subtilis type spore adsorbed on one of the exemplary surfaces, whereas the aspect of spectrum reproducibility on one and several different surfaces is not discussed.

The subject matter of the U.S. Pat. No. 7,583,379 B2 "Surface enhanced Raman spectroscopy (SERS) systems and methods of use thereof" is a SERS substrate for detection of viruses, bacteria and other biological systems, comprising silver, nickel or silicon nanowires fabricated with the above mentioned PVD method and placed on glass or silicon surfaces. The inventors analyze mainly the relationship between the length, diameter and orientation of nanowires in relation to the surface and the intensity of resulting SERS spectra, while not specifying the enhancement factor and assuring at the same time that the spectra are reproducible for one substrate.

The subject matter of international patent application published with the number WO 2009/035479 "Highly efficient surface enhanced Raman and fluorescence nanostructure substrate" is a substrate for SERS measurements composed of, e.g., semiconductor surface with nanowires affixed, the nanowires comprising a core, i.e., $Ga_2O_3$, ZnO, InSb or SiC, with a length from 20 nm to 100 nm and diameter 40 nm, obtained with a VLS method (Vapor-Liquid-Solid mechanism of deposition) and a silver or a gold shell with a thickness from 3 nm to 20 nm. The inventors show that the enhancement factor for rhodamine 6G is 35 times higher than that obtained with a commercially available Mesophotonics substrate for SERS measurements.

The subject matter of international patent application published with the number WO2008/09/4089 "Active sensor surface and a method for manufacture thereof" is a SERS substrate composed of nanowires or nanotubes with a length from 0.1 μm to 100 μm and a diameter from 5 nm to 400 nm, with silver nanoparticles deposited thereon, the nanoparticles ranging from 0.5 nm to 100 nm in size. The inventors indicate only potential use of the substrate in SERS studies while not giving any specific examples.

First information on possible application of gold coated GaN as an SERS-active substrate have been presented in a paper *Porous GaN as a Template to Produce Surface-Enhanced Raman Scattering-Active Surfaces* [T. L. Wiliamson, X. Guo, A. Zukoski, A. Sood, Diego J. Diaz, and P. W. Bohn, *J. Phys. Chem.* B 2005, 109, 20186-20191]. The GaN surface was developed "in depth" by platinum-assisted photo-etching to obtain a porous structure (PGaN). Before etching the surface of GaN specimens was coated with 10 nm platinum films through a mask forming a regular pattern of 0.5 mm diameter circles spaced by 1 mm. The etching was carried out in a solution containing $H_2O_2$, HF and $CH_3OH$ in a 1:2:2 volume ratio under UV irradiation. Following a 90 minutes etching 2-3 μm deep pores with a diameter 80-100 nm were obtained. So prepared GaN surface was coated with gold and silver films with a thickness from 10 nm to 100 nm. Two deposition methods were used, namely an electroless deposition from solution and vacuum evaporation. The enhancement factor (EF) determined by the authors for the surface is $2 \times 10^4$.

So far, no SERS substrate based on a surface of a gallium-containing nitride is known, with the surface developed so that the whiskers of gallium-containing nitride with linear defects inside are formed, possibly put in bunches, subsequently coated with appropriate metal film. The issue is subject of further research by the applicants.

The inventors of the present invention have noticed that such a surface of a gallium-containing nitride coated with appropriate metal film, i.e., gold, silver, platinum, copper and/or alloys thereof, with appropriate thickness, gives reproducible and strong Raman signal enhancement (enhancement factor EF of the order $10^6$) for molecules adsorbed thereon. The enhancement factor is particularly high when the whiskers mentioned are grouped in bunches.

According to the present invention, a surface enhanced Raman scattering substrate comprising a semiconductor surface containing the whiskers defined above, coated with metal selected from the group consisting of silver, gold, platinum, copper and/or alloys thereof, is characterised in that the semiconductor mentioned is a gallium-containing nitride and that essentially each whisker contains a linear defect inside. Here, "essentially each whisker" means that almost all whiskers do contain the defect inside. Still, it is possible that some of whiskers do not contain the defect inside.

Preferably, the whiskers mentioned are connected with each other through terminals distant from the semiconductor surface mentioned, forming conical bunches.

Preferably, the crystalline defect mentioned is a dislocation or an inversion domain.

According to the invention, the film thickness of the metal mentioned on the semiconductor surface mentioned ranges from 50 nm to 150 nm, preferably from 70 nm to 80 nm.

In a preferred embodiment of the invention, the length of the whiskers mentioned ranges from 0.2 μm to 2.0 μm, more preferably from 0.5 μm to 1.5 μm; the diameter of the whiskers ranges from 40 nm to 150 nm, more preferably from 50 nm to 70 nm; and the length to diameter ratio of the whiskers mentioned ranges from 5 to 50, more preferably from 10 to 30.

In turn, the surface density of the whiskers on the semiconductor surface mentioned ranges preferably from $10^8/cm^2$ to $10^{10}/cm^2$.

According to the invention, the metal mentioned is preferably gold, and the gallium containing nitride is preferably gallium nitride GaN.

In a preferred embodiment of the invention, the semiconductor surface of gallium nitride mentioned is a surface similar to a crystallographic plane with Miller indices (0001), i.e., the crystallographic plane C of Ga polarity.

In another preferred embodiment of the invention, the semiconductor surface of gallium nitride mentioned is a surface similar to a crystallographic plane with Miller indices (000-1), i.e., the crystallographic plane C of N polarity.

Here, "similar to a crystallographic plane" means exactly the aforementioned crystallographic plane or a plane very close to that one.

For molecules adsorbed at its surface, the substrate according to the invention has preferably the enhancement factor, EF, higher than $10^4$, and more preferably higher than $10^6$.

The reproducibility of Raman spectra recorded at different points of the same substrate according to the invention is preferably not less than 80%. In turn, the reproducibility of Raman spectra recorded on different substrates according to the invention is not less than 75%.

The substrates according to the invention are characterised by the enhancement factor of the order $10^6$, i.e., by two orders of magnitude higher than that estimated for a commercially available SERS substrate. In addition, the substrate according to the invention is marked by a very good repeatability of recorded spectra both for one (not less than 80%) and for several substrates (not less than 75%).

Definitions and Calculation Methods of Major Parameters

Gallium containing nitride—a compound with a general formula $Al_xGa_{1-x-y}In_yN$, where $0 \leq x \leq 1$, $0 \leq y \leq 1$ and $0 \leq x+y < 1$. The notion of gallium containing nitride covers mixed aluminium gallium indium nitride, in particular AlGaInN, mixed gallium indium nitride, in particular GaInN, and also stoichiometric gallium nitride GaN.

Enhancement Factor; EF— specifies the ratio of integral intensities (intensities at maxima) contributed by molecules adsorbed on the surface and molecules in solution and is defined by the following expression:

$$EF = (I_{SERS}/I_{Raman})/(N_{SERS}/N_{Raman});$$

where:

$I_{SERS}$—measured integral band intensity in SERS spectrum of molecules adsorbed on the surface, $I_{Raman}$—measured integral band intensity in Raman spectrum of molecules in solution, $N_{Raman}$—denotes the number of molecules in solution "illuminated" by laser radiation for recording the Raman spectrum, $N_{SERS}$—denotes the number of adsorbed molecules "illuminated" by laser radiation for recording the SERS spectrum, $N_{Raman}$—was determined using the expression:

$$N_{Raman} = N_A \times C \times D_f \times \pi r^2$$

where:

$N_A$—Avogadro number, $6.02 \times 10^{23}$, c—molar concentration of the solution, $D_f$—focal depth; $Df = 2\lambda/NA^2$, where, for the 785 nm line, NA, i.e., lens aperture, is 0.55 yielding $D_f = 5$ µm $\pi r^2$—geometrical cross section of molecules $N_{SERS}$—was estimated based on the surface coverage, assuming that the molecules are adsorbed on the surface in a form of a monomolecular film, and taking into account the size of area illuminated by the laser.

$$N_{SERS} + N_m \times A$$

where:

$N_m$—number of molecules in the stock solution used for adsorption;

A—area illuminated by the laser, where $A = \pi \times S$, wherein S denotes the size of the laser spot that is 1 µm² for the 785 nm line used in the measurements and the lens magnification 50×.

Reproducibility for One Substrate— means reproducibility of SERS spectra recorded on that substrate at its different points (agreement as to the intensity and band positions in SERS spectra recorded under identical measurement conditions). The parameter has been determined in the following way: the integrals from the area corresponding to the difference between the two comparable spectra recorded on the same substrate but at its different points have been determined. Reproducible spectra (agreement 100%) are deemed those, for which the integrals from the area corresponding to the difference do not differ by more than 3%.

Reproducibility for Different Substrates— means reproducibility of SERS spectra recorded on different substrates (agreement as to the intensity and band positions in SERS spectra recorded under identical measurement conditions). The parameter has been determined in the following way: the integrals from the area corresponding to the difference between the two comparable spectra recorded on different substrates have been determined. Reproducible spectra (agreement 100%) are deemed those, for which the integrals from the area corresponding to the difference do not differ by more than 3%.

Side with Polarity of a Group III Element (Gallium Side):

In the crystals of nitrides of group III elements with a wurtzite structure, crystalline planes perpendicular to the $C_6$ crystal symmetry axis (so called C planes with Miller indices (0001)) are not equivalent. These planes are called polar planes, and the side with polarity of a group III element (in the case of stoichiometric gallium nitride GaN referred to briefly as gallium side) and the side with polarity of N, referred to briefly as nitrogen side. The sides have different physico-chemical properties.

DETAILED DESCRIPTION OF THE INVENTION

Figure 2:
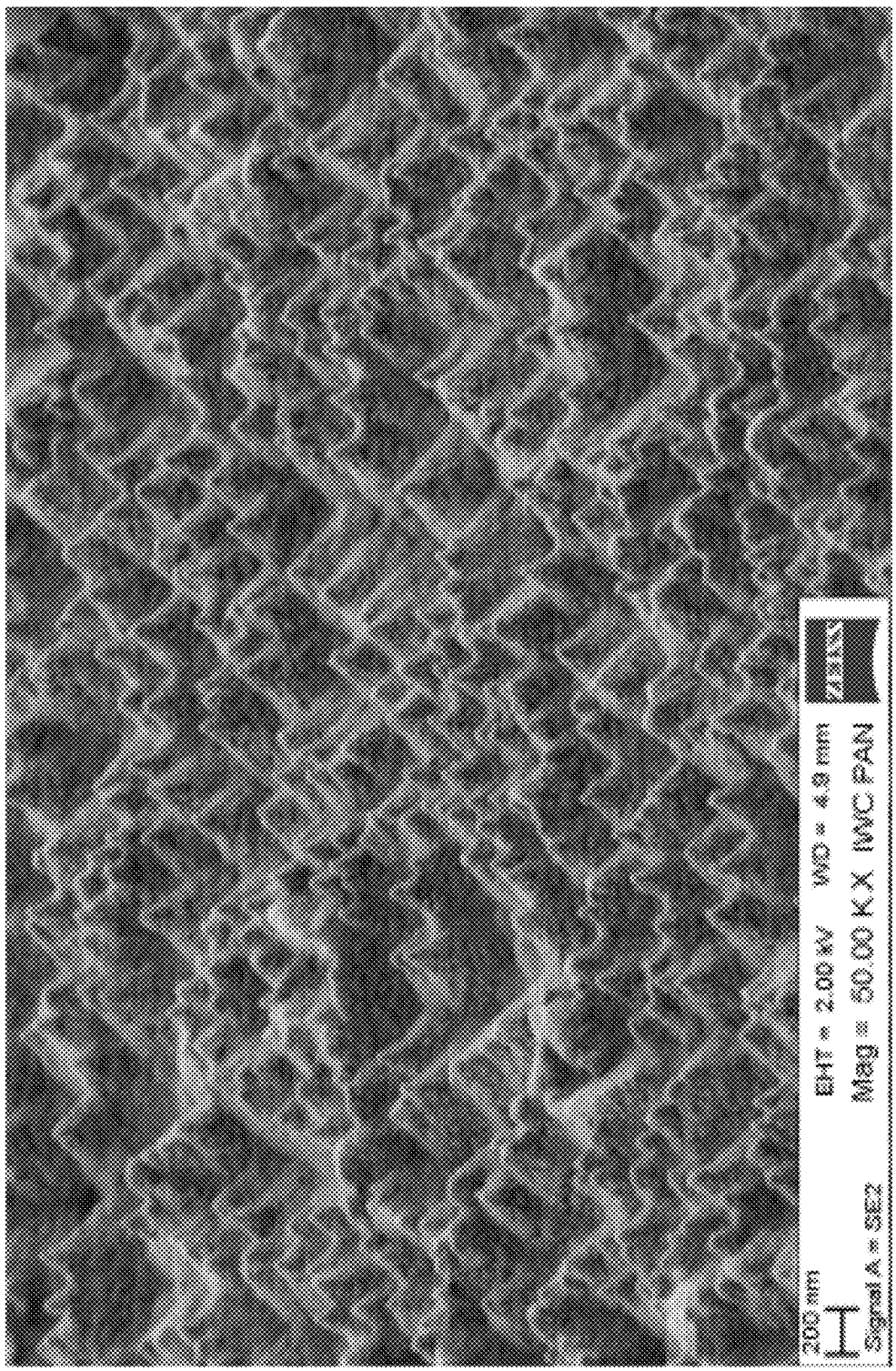
Figure 3A:
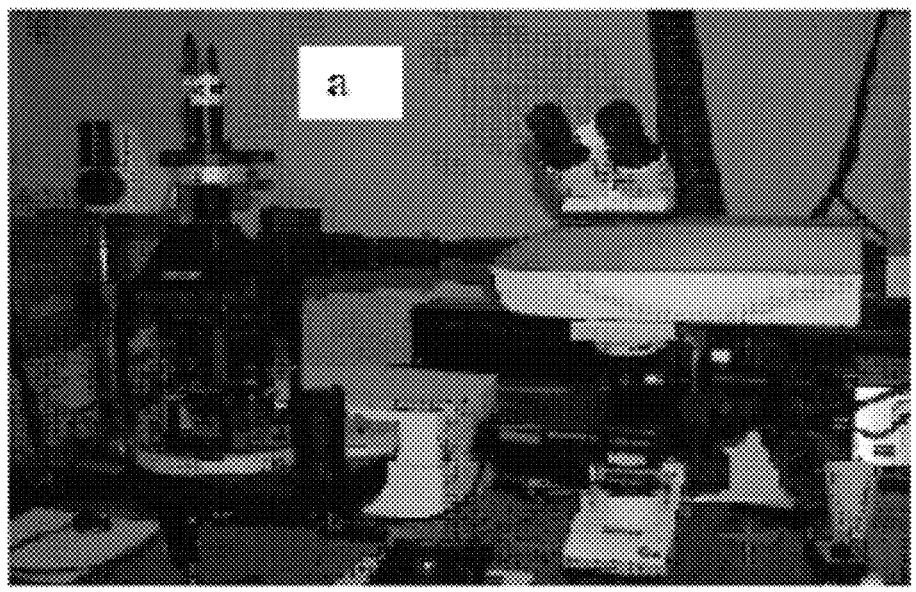
Figure 3B:
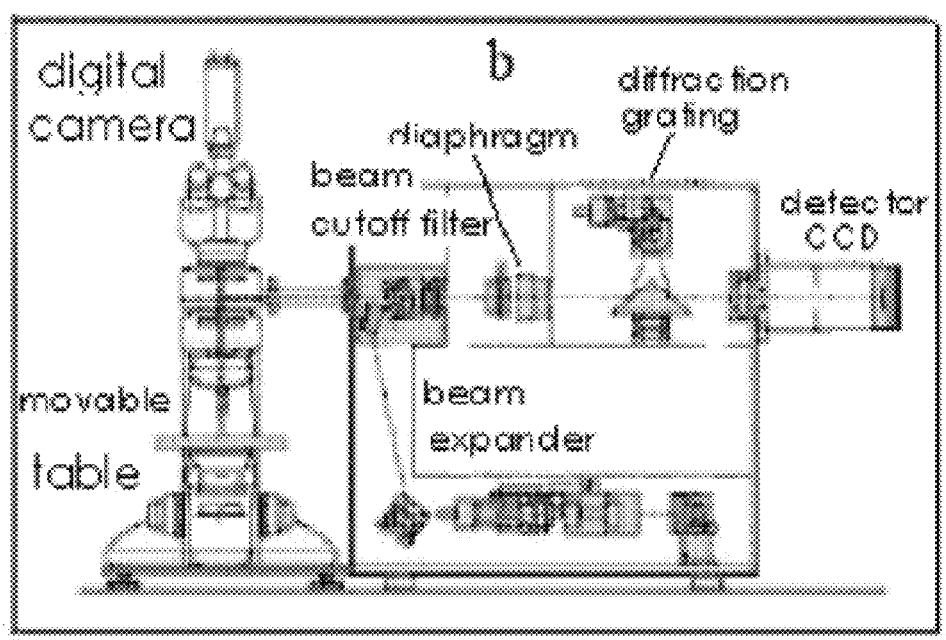
Figure 4:
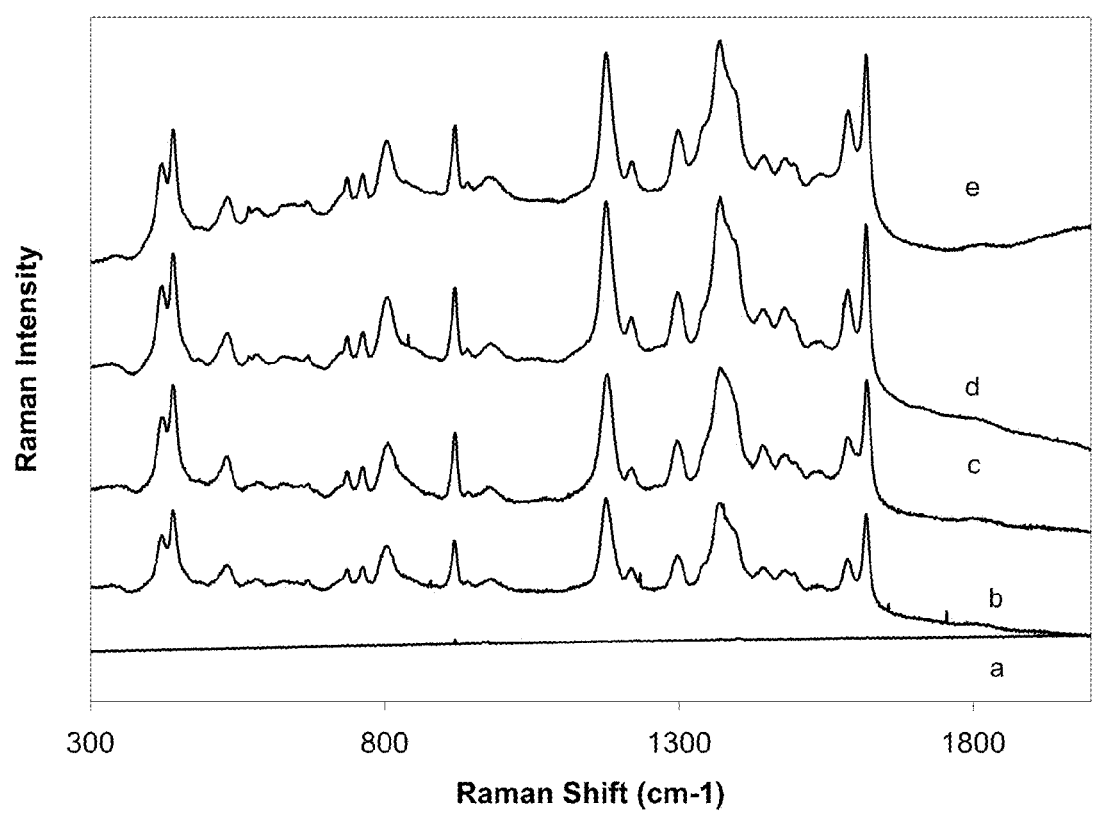
Figure 5A:
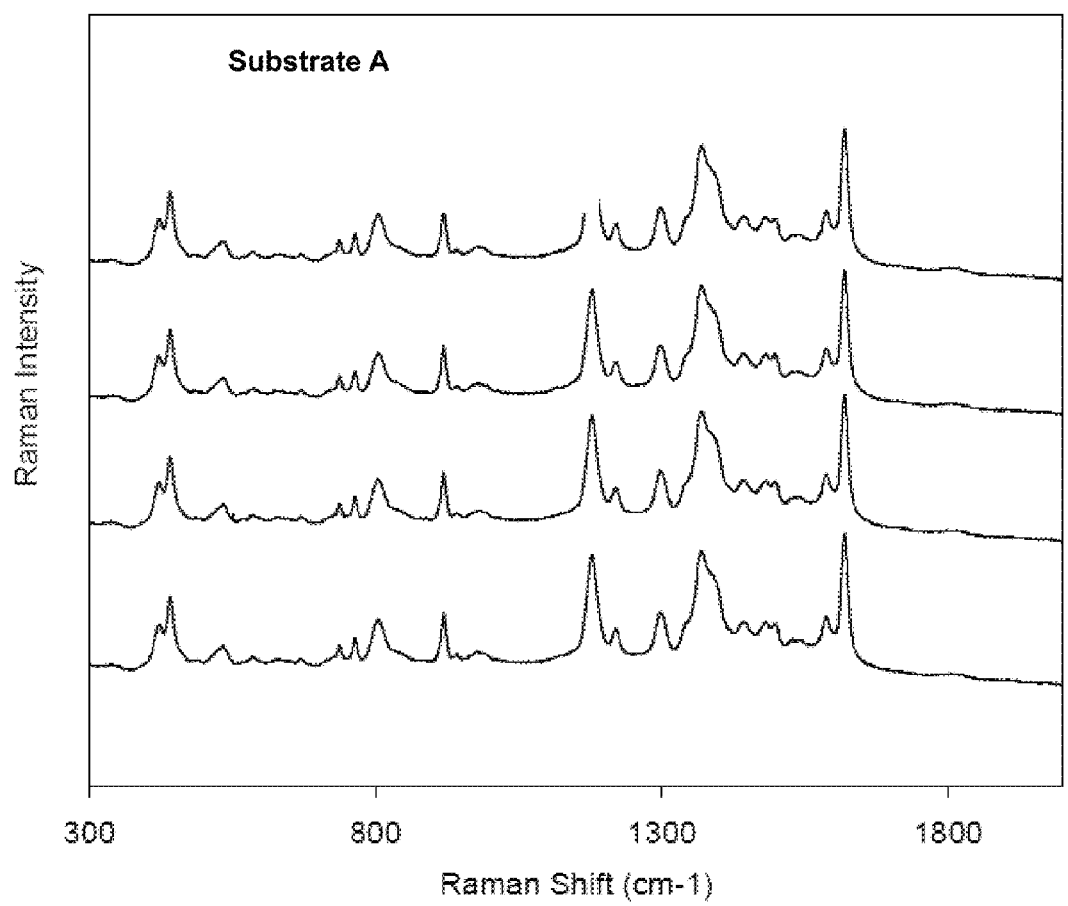
Figure 5B:
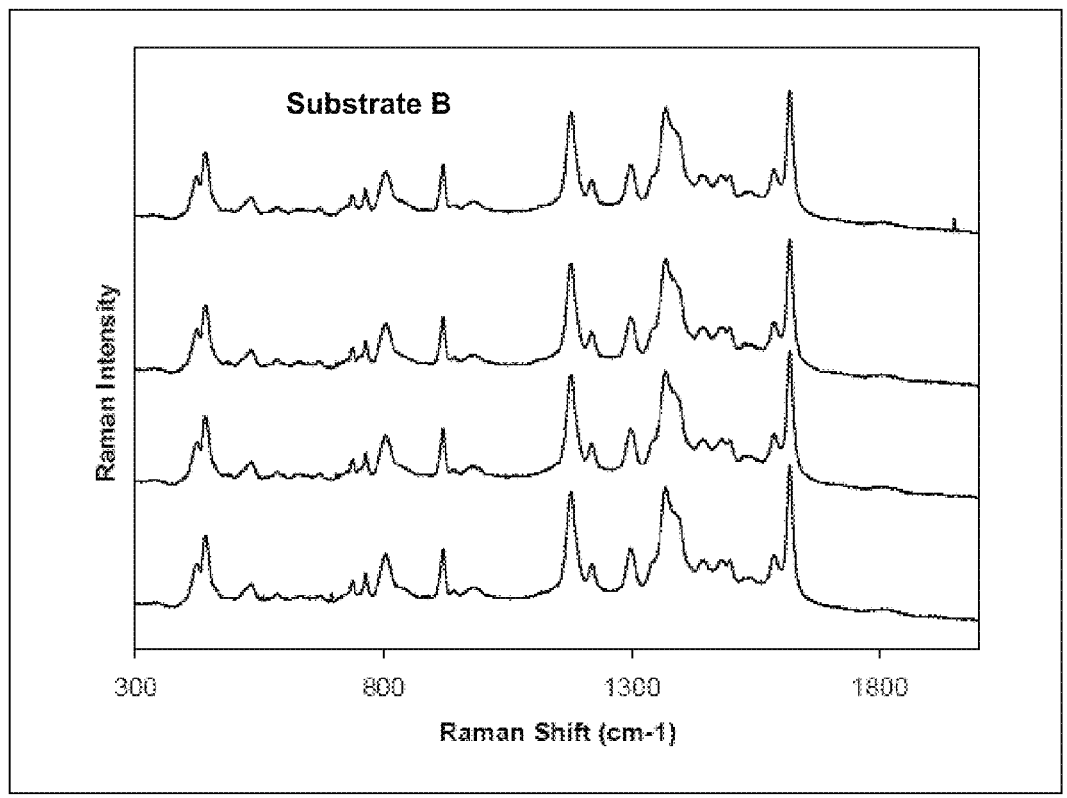
Figure 6:
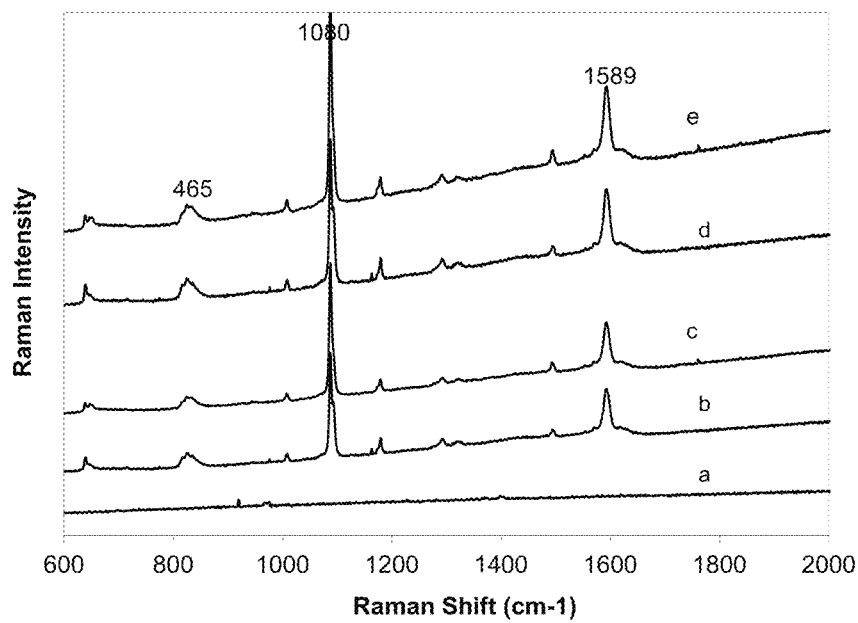
Figure 7:
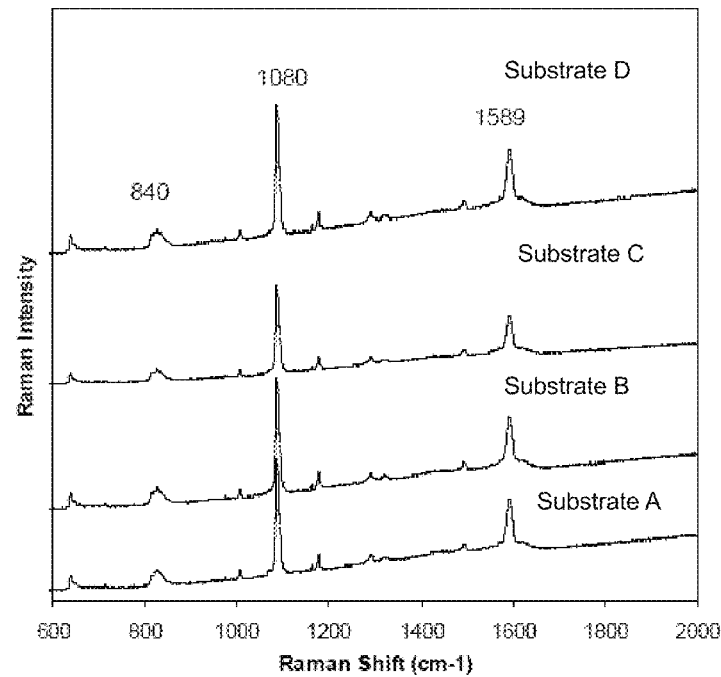
Figure 8:
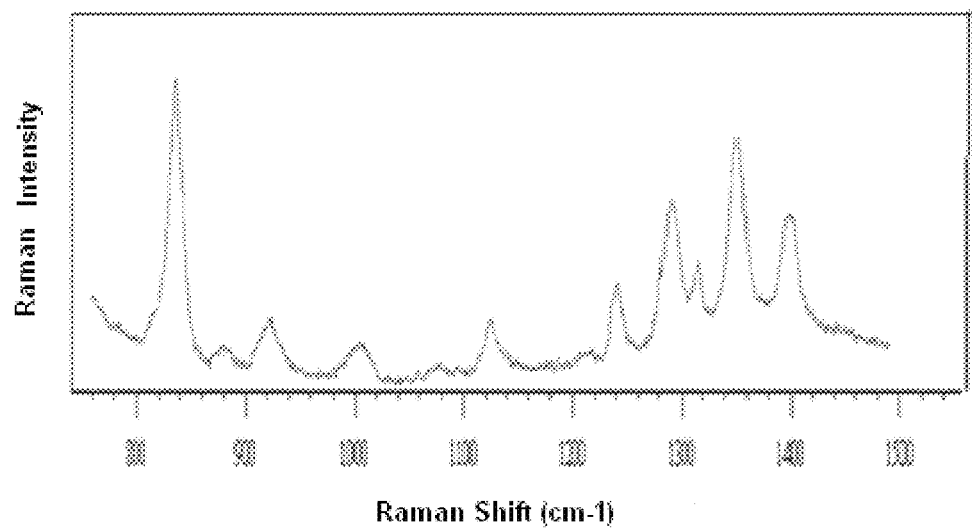
Figure 9:
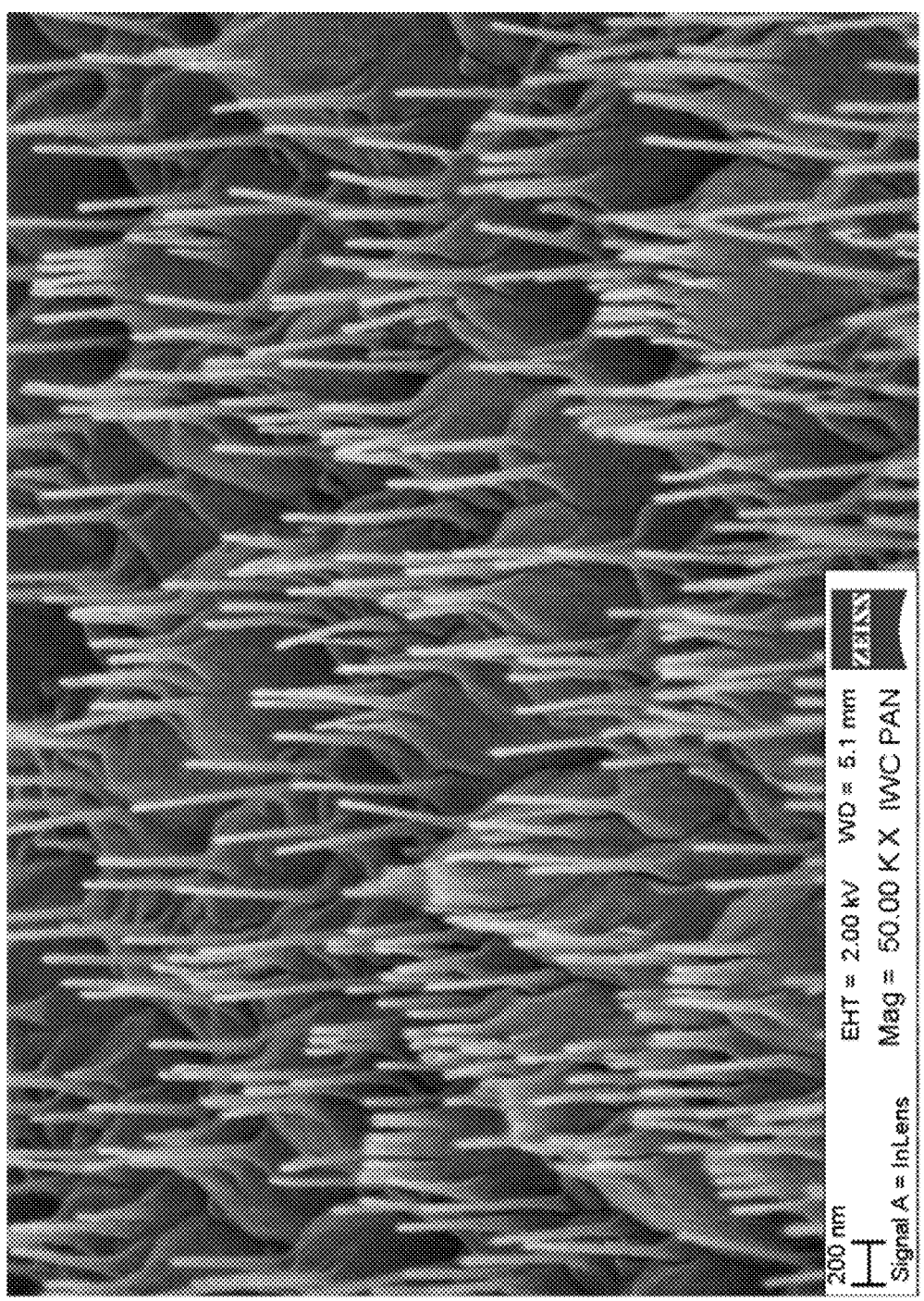

The subject matter of the invention will be described with reference to the drawings where:

FIG. 1 illustrates a SEM picture of GaN surface according to the invention after etching process where the whiskers on the surface form characteristic bunches, FIG. 2 illustrates a SEM picture of GaN surface from FIG. 1 following coating with a 70 nm thick gold film, FIG. 3 illustrates an external view of a Raman microscope used to record SERS spectra (a) and its schematic diagram (b), FIG. 4 illustrates SERS spectra of malachite green (MGTIC), adsorbed from a $10^{-6}$M solution, on a SERS substrate according to the invention, recorded at its different points (b, c, d, e) and the substrate itself (a), FIGS. 5a and 5b illustrate SERS spectra of malachite green (MGTIC), adsorbed from a $10^{-6}$M solution, on two different SERS substrates according to the invention (A and B), recorded at different points on each substrate, respectively, FIG. 6 illustrates SERS spectra of p-aminothiophenol molecules adsorbed from an aqueous $10^{-5}$M solution on a SERS substrate according to the invention, recorded at its different points (a, b, c, d), FIG. 7 illustrates SERS spectra of p-aminothiophenol molecules adsorbed from an aqueous $10^{-5}$M solution on four different SERS substrates according to the invention (A, B, C, D), FIG. 8 illustrates SERS spectrum of L-alanine molecules adsorbed from an aqueous $10^{-4}$M solution on a SERS substrate according to the invention, and FIG. 9 illustrates a SEM picture of another GaN surface according to the invention after etching, where the whiskers on the surface do not form bunches.

PREFERRED EMBODIMENTS

Embodiment 1

A SERS substrate according to the invention has been fabricated as follows:

A 3-8 µm thick GaN film fabricated on sapphire with MOCVD method was used as a substrate. GaN wafers on sapphire were cut in 5×5 mm specimens. The surface of the specimens, similar to the crystal plane C with gallium polarity, was etched for 20 minutes in a 10% aqueous HF solution, and subsequently washed five times in deionised water. After surface cleaning, each specimen was placed in 150 ml of aqueous KOH and $K_2S_2O_8$ solution with concentrations 0.05 mol and 0.03 mol, respectively. Subsequently, the solution with the sample was irradiated for 10 minutes with UV lamp. During the photo-etching, the solution was stirred with a magnetic mixer.

After etching, the sample was triply washed with deionised water, and subsequently water was removed from the surface with a nitrogen jet.

Directly before gold evaporation, the samples were washed for 10 minutes in concentrated HCl. After that period of time the sample was washed in a deionised water jet for 15 s. Water was removed from the surface with a nitrogen jet.

Then a gold film was evaporated onto the surface (using E-gun evaporation in a Denton vacuum evaporator with electron beam heated crucible with metal). According to the invention, the thickness of the metal film is of essential importance, preferably being from 70 nm to 80 nm. More specifically, two plates: a control one (flat) and one being tested (with a surface developed by etching with a method indicated above) are simultaneously (i.e., in the same device and in the same process) coated with a gold film and the thickness 70-80 nm refers to a gold film obtained on the flat control plate.

In that way, a SERS substrate according to the invention comprising a GaN film has been fabricated.

The surfaces of GaN specimens coated with gold film were characterised with scanning electron microscopy (SEM), atomic force microscopy (AFM) and Raman spectroscopy.

Topographic examinations of fabricated surfaces were carried out with a Zeiss Supra scanning microscope. Photographic documentation was obtained by recording secondary electrons with accelerating voltage 2 kV.

After GaN surface development with etching method according to the embodiment 1, the SEM pictures (FIG. 1) reveal approximately 1.5 μm long whiskers with diameter of 60 nm.

After coating the rough GaN surface with a gold film about 70 nm thick, the SEM pictures (FIG. 2) reveal surfaces with a very well developed (roughened) structure. GaN whiskers, stuck together in characteristic bunches by surface tension forces, are coated with gold, forming regularly distributed conical structures with a diameter 300-400 nm at the base.

Embodiment 2

It was proceeded similarly as in the embodiment 1, except for that a 3-8 μm thick $Al_{0.03}Ga_{0.97}N$ film fabricated with MOCVD method on sapphire was used as a substrate. In that way, a SERS substrate according to the invention comprising an $Al_{0.03}Ga_{0.97}N$ film has been fabricated.

Embodiment 3

It was proceeded similarly as in embodiment 1, except for that the etching described was shorter and lasted for 5 minutes. In that way, a SERS substrate according to the invention comprising a GaN film has been fabricated.

After the development of GaN surface with the etching method according to the embodiment 3, SEM pictures (FIG. 9) reveal whiskers that are not connected in bunches.

The following probes have been used to test SERS substrates according to the invention: malachite green (Aldrich, 99.99%), p-aminothiophenol (Aldrich, 99.99%) and aminoacid L-alanine (Aldrich, 99.99%). Enhancement Factors (EF) have been determined for these systems.

Raman spectra were recorded with a high resolution InVia (Ranishaw) confocal Raman microspectrometer. The wavelength of excitation light used in measurements was 785 nm. The scattered light was analysed in the spectrometer with a diffraction grating, and the intensity for each energy was recorded by a sensitive CCD detector. The magnification of the lens focusing the laser beam on the sample was 50×. The spatial resolution was better than 1 μm, and the spectral resolution was about 1 cm$^{-1}$. The power of the laser used for measurements ranged from 1 mW to 3 mW for SERS measurements and 150 mW while recording normal Raman spectra. The spectra were recorded with an accumulation time from 10 to 40 seconds. An external view of the microscope (a) and its schematic diagram (b) are shown in FIG. 3.

2 microliters of a dye—$10^{-6}$M solution of malachite green in chloroform were placed on a SERS substrate according to the embodiment 1. Then, the substrate has been dried and 30 Raman spectra have been recorded at different points of the surface. FIG. 4 shows four randomly selected spectra of malachite green adsorbed on the surface of the substrate (b, c, d, e) and the spectrum of the substrate itself (a) (FIG. 4). The spectra were recorded during 10 s, using a 785 nm excitation with power of 2.5 mW.

In a preferred embodiment, the spectra recorded at different points of the substrate are identical. They include strong bands at frequencies: 1618, 1370, 1180 and 441 cm$^{-1}$, whereas the relative intensities in each recorded spectrum are virtually the same.

Subsequent experiments tested the reproducibility of recorded SERS spectra for different platforms obtained with the same method. The spectra of a dye adsorbed on 10 subsequent SERS substrates, such as those obtained in the embodiment 1, have been recorded. FIG. 5 shows the results obtained for two randomly selected substrates A and B fabricated with a method according to the invention.

In addition, the enhancement factor for malachite green adsorbed on the substrate has been determined with the expression:

$$EF=(I_{SERS}/I_{Raman})/(N_{SERS}/N_{Raman})$$

where:

$I_{SERS}$ and $I_{Raman}$ are measured integral band intensities in the spectra of malachite green molecules adsorbed on a gold coated GaN surface ($I_{SERS}$) and in a $10^{-6}$M malachite green solution ($I_{Raman}$);

$N_{SERS}$ and $N_{Raman}$ denote the numbers of adsorbed malachite green molecules "illuminated" with laser light to obtain SERS spectrum and Raman spectrum, respectively.

$I_{SERS}$ and $I_{Raman}$ were measured for the band at frequency 1180 cm$^{-1}$. $N_{SERS}$ has been estimated based on a surface coverage with malachite green ($1\times10^{14}$ molecules/cm$^2$) [B. Pettinger, B. Ren, G. Picardi, R. Schuster, G. Ertl, *J. Raman Spectrosc*. Volume 36 Issue 6-7, Pages 541-550]. $N_{Raman}$ denotes the number of malachite green molecules in solution under study calculated with the definitions given above.

In a preferred embodiment of the substrate according to the invention, the estimated enhancement factor (EF) for malachite green is $2.6\times10^6$ and is by two orders of magnitude higher than the enhancement factor estimated on a commercially available SERS substrate.

In another preferred embodiment of the invention, p-aminothiophenol molecules have been adsorbed on a SERS platform and the reproducibility of collected spectra has been tested for the same surface and for two different surfaces (FIGS. 6 and 7).

The light wavelength used in measurements was 785 nm, the laser power at the sample was 3 mW and the spectrum accumulation time was about 10 s.

Preferably, the spectra of p-aminothiophenol molecules adsorbed on a SERS substrate from a $10^{-4}$M aqueous p-aminothiophenol solution recorded at different points of the surface are reproducible (FIG. 6). Relative intensities of the bands characteristic for p-aminothiophenol at 840 cm$^{-1}$, 1080 cm$^{-1}$ and 1589 cm$^{-1}$ are reproducible to 80% for all recorded spectra.

Preferably, the frequencies and relative intensities of p-aminothiophenol bands are reproducible for four different SERS substrates fabricated with the same method according to the invention (FIG. 7). The reproducibility of frequencies and relative band intensities is higher than 75% for four substrates A, B, C and D (FIG. 7) fabricated according to the invention.

For the system described above (p-aminothiophenol adsorbed on a SERS substrate) the enhancement factor was estimated using the relationship given above: $EF=(I_{SERS}/I_{Raman})/(N_{SERS}/N_{Raman})$ and was $1.4\times10^6$.

$I_{SERS}$ and $I_{Raman}$ have been estimated for the most intense band appearing at frequency 1589 cm$^{-1}$ ascribed to a $v_{8a}$ vibration of the p-aminothiophenol aromatic ring in SERS and in normal Raman spectrum, respectively. The normal Raman spectrum was recorded for a 10 mM aqueous p-aminothiophenol solution, using 785 nm excitation line and laser power 150 mW. $N_{SERS}$ and $N_{Raman}$ correspond to the numbers of molecules excited with laser beam during SERS measurements and during recording normal Raman spectrum in p-aminothiophenol solution.

In another preferred embodiment, 2 microliters of a $10^{-4}$M aqueous solution of L-alanine were placed on a SERS substrate according to the embodiment 1 and after the substrate had been dried, the SERS have been recorded (FIG. 8). The spectra were recorded with a 785 nm excitation, the laser power was 10 mW, and the spectrum accumulation time was 5 minutes (FIG. 8). In that case, the estimated enhancement factor (EF) for L-alanine was $1.9 \times 10^4$.

Similar measurements performed for substrates according to embodiments 2 and 3 yielded very similar results.

The substrate according to the invention is characterised by a high enhancement factor of the order $10^6$ and a very good reproducibility of recorded spectra both for one (not less than 80%) and for several substrates (not less than 75%).

A substrate according to the invention can be used for SERS studies of a broad range of chemical compounds (e.g., organic compounds including dyes, peptides, natural organic compounds present in live cells, as for instance phenylalanine or DNA, biologically active substances and biological processes, such as for instance in studies on neurotransmitters including catechol, dopamine, epinephrine, nucleotides, nucleosides, membranes and cytochromes). The subject matter of the invention can be also dedicated to the detection and characterisation of viruses, drug interactions with proteins or posttranslational modifications. Due to the properties mentioned above the subject matter of the invention can be used as an active platform in biosensor design, making SERS technique a useful analytical tool in medical diagnostics.

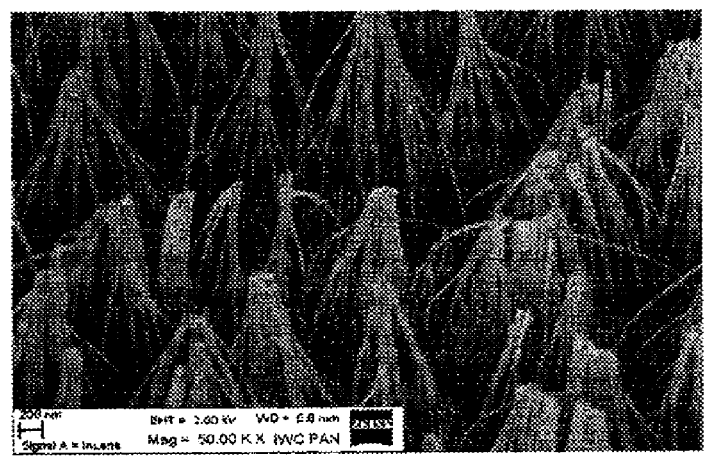

The invention claimed is:

1. A substrate for surface enhanced Raman scattering studies comprising a semiconductor surface containing whiskers, wherein:
   the whiskers are coated with at least one metal selected from the group consisting of silver, gold, platinum, copper and alloys thereof,
   the semiconductor is a gallium-containing nitride and essentially each whisker contains a linear defect inside.

2. The substrate of claim 1, wherein the whiskers are connected with each other through terminals distant from the semiconductor surface, forming conical bunches.

3. The substrate of claim 1, wherein the linear defect is a dislocation or an inversion domain.

4. The substrate of claim 1, wherein the film thickness of the metal on the semiconductor surface ranges from 50 nm to 150 nm.

5. The substrate of claim 1, wherein the length of the whiskers ranges from 0.2 µm to 2.0 µm.

6. The substrate of claim 1, wherein the diameter of the whiskers ranges from 40 nm to 150 nm.

7. The substrate of claim 1, wherein the length to diameter ratio of the whiskers ranges from 5 to 50.

8. The substrate of claim 1, wherein the surface density of the whiskers on the semiconductor surface ranges from $10^8$/cm$^2$ to $10^{10}$/cm$^2$.

9. The substrate of claim 1, wherein the metal is gold.

10. The substrate of claim 1, wherein the gallium-containing nitride is gallium nitride.

11. The substrate of claim 10, wherein the semiconductor surface of gallium nitride is a surface similar to a crystallographic plane with Miller indices (0001).

12. The substrate of claim 10, wherein the semiconductor surface of gallium nitride is a surface similar to a crystallographic plane with Miller indices (000-1).

13. The substrate of claim 1, wherein for molecules adsorbed at its surface, the enhancement factor, EF, is higher than $10^4$.

14. The substrate of claim 1, wherein the reproducibility of Raman spectra recorded at different points of the same substrate is not less than 80%.

15. The substrate of claim 1, wherein the reproducibility of Raman spectra recorded on different substrates is not less than 75%.

16. The substrate of claim 1, wherein the film thickness of the metal on the semiconductor surface ranges from 70 nm to 80 nm.

17. The substrate of claim 1, wherein the length of the whiskers ranges from 0.5 µm to 1.5 µm.

18. The substrate of claim 1, wherein the diameter of the whiskers ranges from 50 nm to 70 nm.

19. The substrate of claim 1, wherein the length to diameter ratio of the whiskers ranges from 10 to 30.

20. The substrate of claim 1, wherein for molecules adsorbed at its surface, the enhancement factor, EF, is higher than $10^6$.

21. The substrate of claim 2, wherein the linear defect is a dislocation or an inversion domain.

* * * * *

UNITED STATES PATENT AND TRADEMARK OFFICE
CERTIFICATE OF CORRECTION

| | |
|---|---|
| PATENT NO. | : 8,531,660 B2 |
| APPLICATION NO. | : 13/051618 |
| DATED | : September 10, 2013 |
| INVENTOR(S) | : Dziecielewski |

It is certified that error appears in the above-identified patent and that said Letters Patent is hereby corrected as shown below:

Please delete the title page and insert the title page showing an illustrative figure as attached.

Signed and Sealed this
Eighth Day of April, 2014

Michelle K. Lee
*Deputy Director of the United States Patent and Trademark Office*

(12) United States Patent
Dziecielewski et al.

(10) Patent No.: US 8,531,660 B2
(45) Date of Patent: Sep. 10, 2013

(54) SUBSTRATE FOR SURFACE ENHANCED RAMAN SCATTERING STUDIES

(75) Inventors: Igor Dziecielewski, Warsaw (PL); Robert Holyst, Warsaw (PL); Agnieszka Kaminska, Sulejowek (PL); Sylwester Porowski, Warsaw (PL); Tadeusz Suski, Warsaw (PL); Jan Weyher, Warsaw (PL)

(73) Assignees: Instytut Chemii Fizycznej Polskiej Akademii Nauk, Warsaw (PL); Instytut Wysokich Cisnien Polskiej Akademii Nauk, Warsaw (PL)

( * ) Notice: Subject to any disclaimer, the term of this patent is extended or adjusted under 35 U.S.C. 154(b) by 377 days.

(21) Appl. No.: 13/051,618

(22) Filed: Mar. 18, 2011

(65) Prior Publication Data
US 2011/0235031 A1   Sep. 29, 2011

(30) Foreign Application Priority Data

Mar. 23, 2010   (PL) .................................. 390798

(51) Int. Cl.
*G01J 3/44* (2006.01)

(52) U.S. Cl.
USPC ............................................. 356/301

(58) Field of Classification Search
USPC ............................................. 356/301
See application file for complete search history.

(56) References Cited

U.S. PATENT DOCUMENTS

| | | |
|---|---|---|
| 6,329,215 B1 | 12/2001 | Porowski et al. |
| 7,583,379 B2 | 9/2009 | Zhao et al. |
| 7,586,601 B2 | 9/2009 | Ebstein |
| 7,595,872 B2 | 9/2009 | Premasiri et al. |
| 7,639,356 B2 | 12/2009 | Prokes et al. |
| 7,715,003 B2 | 5/2010 | Mazur et al. |
| 7,867,770 B2 | 1/2011 | Premasiri |
| 2006/0275541 A1 | 12/2006 | Weiner |
| 2008/0096005 A1 | 4/2008 | Premasiri |
| 2008/0266555 A1 | 10/2008 | Murphy et al. |
| 2008/0285024 A1 | 11/2008 | Prokes et al. |
| 2009/0279085 A1 | 11/2009 | Ebstein |
| 2010/0035412 A1* | 2/2010 | Samuelson et al. ......... 438/478 |
| 2010/0129623 A1 | 5/2010 | Johansson et al. |
| 2010/0171948 A1 | 7/2010 | Mazur et al. |
| 2010/0190661 A1* | 7/2010 | Lee et al. ....................... 506/18 |

FOREIGN PATENT DOCUMENTS

| | | |
|---|---|---|
| PL | 183687 B1 | 12/1998 |
| WO | 2008/094089 A1 | 8/2008 |
| WO | 2009/035479 A1 | 3/2009 |

OTHER PUBLICATIONS

Search Report of P.390798, date of mailing Jun. 11, 2010.
Gang L. Liu et al. "Magnetic Nanocrescents as Controllable Surface-Enhanced Raman Scattering Nanoprobes for Biomolecular Imaging", Advanced Materials 2005, vol. 17, pp. 2683-2688.
Katrin Domke et al. "Tip-Enhanced Raman Spectra of Picomole Quantities of DNA Nucleobases at Au(111)", J. Am. Chem. Soc. 2007, vol. 129, pp. 6708-6709.

(Continued)

*Primary Examiner* — Kara E Geisel
(74) *Attorney, Agent, or Firm* — Westerman Hattori Daniels & Adrian, LLP

(57) ABSTRACT

The invention relates to a substrate for surface enhanced Raman scattering studies comprising a semiconductor surface with whiskers, coated with metal selected from the group consisting of silver, gold, platinum, copper and/or alloys thereof, where the semiconductor mentioned is a gallium-containing nitride and essentially each whisker contains a linear defect inside.

21 Claims, 9 Drawing Sheets